(12) United States Patent
Dockal et al.

(10) Patent No.: US 9,566,364 B2
(45) Date of Patent: Feb. 14, 2017

(54) PREPARATIONS BASED ON FIBRINOGEN AND SULFATED POLYSACCHARIDES

(75) Inventors: Michael Dockal, Vienna (AT);
Friedrich Scheiflinger, Vienna (AT);
Hans Christian Hedrich, Vienna (AT);
Klaus Tschetschkowitsch, Vienna (AT);
Andreas Goppelt, Vienna (AT)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 422 days.

(21) Appl. No.: 12/636,620

(22) Filed: Dec. 11, 2009

(65) Prior Publication Data

US 2010/0166834 A1    Jul. 1, 2010

Related U.S. Application Data

(60) Provisional application No. 61/121,808, filed on Dec. 11, 2008.

(51) Int. Cl.
| | | |
|---|---|---|
| *A61L 24/10* | (2006.01) | |
| *A61L 24/08* | (2006.01) | |
| *A61L 24/04* | (2006.01) | |

(52) U.S. Cl.
CPC ............ *A61L 24/106* (2013.01); *A61L 24/043* (2013.01); *A61L 2400/04* (2013.01)

(58) Field of Classification Search
CPC .............................. A61L 24/106; A61L 24/043
See application file for complete search history.

(56) References Cited

U.S. PATENT DOCUMENTS

| 5,631,011 A | * | 5/1997 | Wadstrom ............ A61K 38/363 |
| | | | 424/400 |
| 6,056,970 A | * | 5/2000 | Greenawalt et al. ......... 424/426 |
| 2005/0282771 A1 | | 12/2005 | Johnson |
| 2007/0110813 A1 | * | 5/2007 | Ingenito et al. ............. 424/488 |

FOREIGN PATENT DOCUMENTS

CN            1788802 A       6/2006

OTHER PUBLICATIONS

Li, B., et al. 2008 Molecules 13: 1671-1695.*
International Search Report and Written Opinion of PCT/EP2009/066897 mailed on Oct. 21, 2010, 10 pages.

* cited by examiner

*Primary Examiner* — Marsha Tsay
(74) *Attorney, Agent, or Firm* — Kilpatrick Townsend & Stockton LLP (57) ABSTRACT

The present invention provides a preparation comprising fibrinogen and a sulfated polysaccharide as a one component composition or as a kit of parts comprising fibrinogen and sulfated polysaccharide as separated components.

The present invention further provides a fibrin clot like structure obtainable by a defined process, a hemostatic patch, a two-component syringe system and various uses of the described preparations, fibrin clot like structures and patches.

32 Claims, 5 Drawing Sheets

PREPARATIONS BASED ON FIBRINOGEN AND SULFATED POLYSACCHARIDES

FIELD OF THE INVENTION

The invention relates to preparations comprising fibrinogen and a sulfated polysaccharide, fibrin-clot like structures obtained thereof, hemostatic patches, and methods of using these.

BACKGROUND OF THE INVENTION

Tissue adhesives based on fibrinogen are employed for seamless and/or seam-supporting binding of human or animal tissue or organ parts, for wound sealing, hemostasis and promoting wound healing. Their mode of action is based on the fact that the (soluble) fibrinogen contained in a ready-to-use, liquid tissue adhesive is converted by thrombin into (insoluble) fibrin. Factor XIII may also be included in the liquid tissue adhesive, where it is activated to Factor XIIIa, by the action of thrombin. This crosslinks the formed fibrin to form a high MW polymer which may improve the effectiveness of the tissue adhesive. The required thrombin activity can either originate from the tissue (the wound surface) to be adhered or can be added in the form of a thrombin and $Ca^{2+}$ ion-containing solution to the tissue adhesive in the course of the sealing. Tissue adhesives based on fibrinogen are known from AT-B-359 653, AT-B-359 652 and AT-B-369 990. Aside from fibrinogen and Factor XIII they may also contain further proteins such as fibronectin and albumin and optionally antibiotic agents. U.S. Pat. No. 5,962,405 (Seelich; Immuno AG) discloses storage-stable fibrinogen preparations in lyophilized form or a form resulting from deep-freezing liquid preparations (deep-frozen) which can be reconstituted and liquefied quickly and in a simple manner to form ready-to-use fibrinogen and/or tissue adhesive solutions. Such preparations are marketed as TISSEEL® fibrin sealant by Baxter Healthcare Corporation (CA, USA).

Hemostatic patches, such as those made from collagen, may be used for sealing tissue and controlling bleeding in a variety of surgical procedures. They can be used with a coating of tissue adhesive, such as fibrin glue. Alternatively, hemostatic patches made from a collagen sponge coated with thrombin and fibrinogen are available, such as TACHOCOMB® hemostatic patches or TACHOSIL® hemostatic patches (Nycomed).

Fibrin sealants and hemostatic patches permit safe hemostasis, good adherence of the seal to the wound and/or tissue areas, high strength of the adhesions and/or wound sealings, complete resorbability of the adhesive in the course of the wound healing process, and may have wound healing promoting properties. Nevertheless, it is usually necessary to hold sealed tissue parts in the desired position for several minutes to ensure that the setting fibrin sealant adheres firmly to the surrounding tissue. Compounds improving the fibrin clot formation and/or strengthening the fibrin clot structure could improve fibrin sealants and hemostatic patches. For example, a strengthened clot would be less prone to fibrinolysis and would be more stable and longer lasting.

The listing or discussion of a prior-published document in this specification should not be taken as an acknowledgement that the document is part of the state of the art or is common general knowledge.

SUMMARY OF THE INVENTION

In a first aspect the present invention provides a preparation comprising fibrinogen and a sulfated polysaccharide as a one component composition or as a kit of parts comprising fibrinogen and sulfated polysaccharide as separated components.

In a second aspect the present invention provides a fibrin clot like structure obtainable by a process comprising the steps of
(a) providing a preparation of the present invention as a solution,
(b) providing a cation containing solution as a separate component, optionally containing thrombin, or as a solution together with the sulfated polysaccharide component of the present invention, optionally containing thrombin,
(c) optionally providing a thrombin solution, and
(d) mixing (a) and (b) and optionally (c) either simultaneously or subsequently in any order so that a fibrin clot like structure is obtained.

In a third aspect the present invention provides a hemostatic patch comprising
(1) a carrier, and
(2) at least one hemostatic agent which is a sulfated polysaccharide, wherein, if the carrier is a sulfated polysaccharide, it is not the same sulfated polysaccharide as the hemostatic agent.

In a fourth aspect the present invention provides a two-component syringe system comprising EITHER
(a) the one component composition of claim 1 in the first barrel, and
(b) a cation containing preparation, optionally together with thrombin, in the second barrel;
OR
(a') the separated sulfated polysaccharide of claim 1 and a cation-containing preparation, optionally together with thrombin in the first barrel, and
(b') a fibrinogen preparation in the second barrel.

In a fifth aspect the present invention provides the use of a preparation of the present invention, a fibrin clot like structure of the present invention or a patch of the present invention for enhancing hemostasis.

In a sixth aspect the present invention provides the use of a preparation of the present invention, a fibrin clot like structure of the present invention or a patch of the present invention for wound healing.

In a seventh aspect the present invention provides the use of a preparation of the present invention, a fibrin clot like structure of the present invention or a patch of the present invention for use as a drug delivery system.

In an eighth aspect the present invention provides a method of tissue sealing or tissue gluing comprising applying on a wound surface a preparation of the present invention, a fibrin clot like structure of the present invention or a patch of the present invention

DETAILED DESCRIPTION OF PREFERRED EMBODIMENTS OF THE INVENTION

In a first aspect the present invention provides a preparation comprising fibrinogen and a sulfated polysaccharide as a one component composition or as a kit of parts comprising fibrinogen and sulfated polysaccharide as separated components.

Fibrinogen preparations are well known in the prior art. Typically, the fibrinogen preparation is a lyophilised preparation or a frozen solution. Suitable preparations may be made as described in U.S. Pat. No. 5,962,405, which discloses substances to increase the solubility of the fibrinogen, lower the liquefaction temperature of concentrated deep-frozen fibrinogen and/or tissue adhesive solutions as well as their viscosity at room temperature. Such substances include benzene, pyridine, piperidine, pyrimidine, morpholine, pyrrole, imidazole, pyrazole, furan, thiazole, purine compounds or vitamins, nucleic bases, nucleosides or nucleotides, preferably in the amount of 0.03 mmol to 3 mmol, most preferably in an amount of 0.07 mmol to 1.4 mmol, per g fibrinogen. Among these substances are, for example, benzoic acid, p-aminobenzoic acid (vitamin H'), p-aminosalicyclic acid, hydroxybenzoic acid, hydroxysalicylic phenylalanine, procaine, niacin, niacinamide, picolinic acid, vitamin $B_6$ (pyridoxin), hydroxypyridines, pyridine dicarboxylic acid, pyridine sulfonic acid, piperidine carboxylic acid ester, pyrimidine, barbituric acid, uracil, uridine, uridine phosphate, thymine, cytosine, cytidine, hydroxypyrimidine, thiamine (vitamin $B_1$), morpholine, pyrrolidone, imidazole, histidine, hydantoin, pyrazole dicarboxylic acid, phenazone, adenosine, adenosine phosphate, inosine, guanosine phosphate, α-furoic acid (furan-2-carboxylic acid), ascorbic acid (vitamin C) and xantosine. Particularly preferred substances are histidine and niacinamide. Other components which are of utility in the tissue adhesive solution, such as those discussed in relation to the first aspect of the invention, may be included in the fibrinogen preparation.

If the fibrinogen preparation is lyophilised, it must be reconstituted. This is typically achieved by adding water, typically water for injection, or a solution. The solution may provide useful solutes such as aprotinin, which is an inhibitor of fibrinolysis. Warming and/or agitation or stirring may be applied to improve reconstitution of the tissue adhesive solution. Where the fibrinogen preparation is frozen, it is typical to warm the preparation to de-frost it, whereupon it becomes the tissue adhesive solution. However, additional material may be added to the fibrinogen preparation during or after de-frosting.

Suitable fibrinogen solutions and methods of making them are described in U.S. Pat. No. 5,962,405. Ready-to-use fibrinogen solutions generally contain 60-120 mg fibrinogen per ml. The fibrinogen component may optionally further contain Factor XIII, and optionally fibronectin or small amounts of plasminogen which can be advantageous in the course of wound healing. A plasminogen activator inhibitor and plasmin inhibitor may also optionally be included, such as aprotinin, $\alpha_2$-plasmin inhibitor, $\alpha_2$-macroglobulin and the like. Generally, these components are optionally included in the fibrinogen solution. Fibrinogen solutions generally do not contain free calcium ions, as these might cause activation of residual traces of prothrombin and hence premature, unwanted clotting. Typically, a calcium chelating agent is included in tissue adhesive solutions to complex residual calcium ions. Suitably, citrate is included as such an agent in the form of a physiologically acceptable salt, such as tri-sodium citrate. Accordingly, the ready-to-use fibrinogen solution generally contains 70-120 mg fibrinogen, optionally 0.5-50 U Factor XIII, optionally 0.5 to 15 mg fibronectin, 0 to 150 μg plasminogen and 0 to 20,000 KIU aprotinin, preferably 1,000 to 15,000 KIU aprotinin, per ml. An exemplary tissue adhesive solution is the sealer protein solution of the TISSEEL® fibrin sealant (Baxter Healthcare Corporation, CA), which comprises 67-106 mg/ml human fibrinogen, 2250-3750 KIU/ml aprotinin fibrinolysis inhibitor, human albumin, 25 mmol/l tri-sodium citrate, histidine, niacinamide, polysorbate 80 and water for injection.

The term "polysaccharide", as used herein, refers to a polymer comprising a plurality (i.e., two or more) of covalently linked saccharide residues. Linkages may be natural or unnatural. Natural linkages include, for example, glycosidic bonds, while unnatural linkages may include, for example, ester, amide, or oxime linking moieties. Polysaccharides may have any of a wide range of average molecular weight (MW) values, but generally are of at least about 300 daltons. For example, the polysaccharides can have molecular weights of at least about 500, 1000, 2000, 4000, 6000, 8000, 10,000, 20,000, 30,000, 50,000, 100,000, 500,000 daltons or even higher. The molecular weight of a polysaccharide may be determined by high performance size exclusion chromatography. Polysaccharides may have straight chain or branched structures. Polysaccharides may include fragments of polysaccharides generated by degradation (e.g., hydrolysis) of larger polysaccharides. Degradation can be achieved by any of a variety of means known to those skilled in the art, including treatment of polysaccharides with acid, base, heat, or enzymes to yield degraded polysaccharides. Polysaccharides may be chemically altered and may have modifications, including but not limited to, sulfation, polysulfation, esterification, and methylation.

In principle, any free hydroxyl group on a monosaccharide component of a polysaccharide can be modified by sulfation to produce a sulfated polysaccharide for potential use in the practice of the invention. For example, such sulfated polysaccharides may include without limitation sulfated mucopolysaccharides (D-glucosamine and D-glucuronic acid residues), curdlan (carboxymethyl ether, hydrogen sulfate, carboxymethylated curdlan) (Sigma-Aldrich), sulfated schizophyllan (Itoh et al. (1990) Int. J. Immunopharmacol. 12:225-223; Hirata et al. (1994) Pharm. Bull. 17:739-741), sulfated glycosaminoglycans, sulfated polysaccharide-peptidoglycan complex, sulfated alkyl maltooligosaccharide (Katsuraya et al. (1994) Carbohydr Res. 260:51-61), amylopectin sulfate, N-acetyl-heparin (NAH) (Sigma-Aldrich), N-acetyl-de-O-sulfated-heparin (NA-de-o-SH) (Sigma-Aldrich), de-N-sulfated-heparin (De-NSH) (Sigma-Aldrich), and De-N-sulfated-acetylated-heparin (De-NSAH) (Sigma-Aldrich).

As a class, sulfated polysaccharides are characterized by a plethora of biological activities with often favorable tolerability profiles in animals and humans. These polyanionic molecules are often derived from plant and animal tissues and encompass a broad range of subclasses including heparins, glycosaminoglycans, fucoidans, carrageenans, pentosan polysulfates, and dermatan or dextran sulfates (Toida et al. (2003) Trends in Glycoscience and Glycotechnology 15:29-46). Lower molecular weight, less heterogeneous, and chemically synthesized sulfated polysaccharides have been reported and have reached various stages of drug development (Sinay (1999) Nature 398:377-378; Orgueira et al. (2003) Chemistry 9:140-169; Williams et al. (1998) Gen. Pharmacol. 30:337-341).

Suitably, the preparation comprises 0.01 μg to 5000 μg sulfated polysaccharide for every mg of fibrinogen. Typically, the preparation comprises 0.01, 0.02, 0.05, 0.10, 0.15, 0.25. 0.5, 1, 2, 5, 10, 20, 50, 100, 200 or 300 μg sulfated polysaccharide for every mg of fibrinogen.

In a second aspect the present invention provides a fibrin clot like structure obtainable by a process comprising the steps of
(a) providing a preparation of the present invention as a solution,
(b) providing a cation containing solution as a separate component, optionally containing thrombin, or as a solution together with the sulfated polysaccharide component of the present invention, optionally containing thrombin,
(c) optionally providing a thrombin solution, and (d) mixing (a) and (b) and optionally (c) either simultaneously or subsequently in any order so that a fibrin clot like structure is obtained.

The cation is at least divalent, preferably from the group consisting of calcium, magnesium, barium and strontium, most preferred calcium, e.g. $CaCl_2$.

A fibrin clot like structure can be obtained by mixing (simultaneously or subsequently in any order) a fibrinogen solution, a sulfated polysaccharide solution, a cation, e.g. calcium ion, containing solution, optionally together with a thrombin solution so that a fibrin clot like structure is formed.

A fibrin clot like structure can also be obtained by mixing (simultaneously or subsequently in any order) a fibrinogen and sulfated polysaccharide containing solution, a cation, e.g. calcium ion, containing solution, optionally together with a thrombin solution so that a fibrin clot like structure is formed.

A fibrin clot like structure can also be obtained by mixing (simultaneously or subsequently in any order) a fibrinogen solution, a sulfated polysaccharide and a cation, e.g. calcium ion, containing solution, optionally together with a thrombin solution so that a fibrin clot like structure is formed.

A fibrin clot like structure can also be obtained by mixing (simultaneously or subsequently in any order) a fibrinogen solution, a sulfated polysaccharide solution either as separated solutions or as one solution and thrombin and cation, e.g. calcium, containing solution so that a fibrin clot like structure is formed.

The thrombin may be provided as a lyophilised preparation or a frozen solution. A lyophilised preparation may be reconstituted by adding water or a solution, with or without warming and/or agitation/stirring. Typically, calcium ions in the form of a physiologically acceptable salt are included in the lyophilizate, or included in the solution used to reconstitute the thrombin preparation. A frozen solution is typically defrosted to provide the thrombin solution, although additional substances such as $CaCl_2$ may be added during or after defrosting.

Typically, the thrombin solution comprises calcium ions, suitably $CaCl_2$, preferably at a concentration of 36-44 μmol/mL.

The thrombin solution containing the required thrombin activity may originate from the tissue (wound surface) to be sealed or it may be added exogenously. Suitable exogenous thrombin solutions are known in the art. The optimal thrombin concentration of a thrombin solution used to form a fibrin sealant depends on the clinical indication, but typically ranges from 1 to 1000 IU/ml. Thrombin activity of a thrombin containing solution is nowadays compared against the second international standard, which has by definition 110 IU/ampoule (Whitton et al, Thromb Haemost 2005; 93: 261-6). Several assays for analyzing thrombin activity are available, including clotting based and chromogenic tests (Gaffney and Edgell, Thromb Haemost 1995; 74: 900-3). In order to achieve fast hemostasis, high thrombin concentrations leading to practically instantaneous clotting are used. Examples are the thrombin solution of the TISSEEL® fibrin sealant (Baxter Healthcare Corporation, CA), which comprises 400-625 IU/ml human thrombin and the thrombin solution of QUIXIL® fibrin sealant and EVICEL® fibrin sealant (Omrix) with 1000 IU/ml activity of human thrombin. If the intention is to use the fibrin sealant as a glue (e.g. in cosmetic or reconstructive surgery), lower thrombin concentrations are used in order to allow the surgeon more time for manipulations before clotting occurs. For such indications, a fibrin sealant variant containing a 4 IU/ml thrombin is on the market in many countries. Fibrin sealants with much lower thrombin concentrations (less than 1 IU/ml) have not been practical in the past, because the clotting time would be too long. However, where a sulfated polysaccharide is included according to the first aspect of the invention, it may be practicable to use a thrombin solution having a low thrombin concentration, such as 1 IU/ml. Thrombin solutions and methods of making them are disclosed in U.S. Pat. No. 5,714,370 (Eibl and Linnau; Immuno AG). In the method of the first aspect of the invention, the calcium ions are typically provided in the thrombin solution. Calcium ions are typically provided as $CaCl_2$, but other soluble and physiologically compatible calcium salts such as calcium lactate and/or calcium gluconate could be used in addition to or as an alternative to $CaCl_2$. The concentration of calcium in the thrombin solution is typically about 40 mM. For example, TISSEEL® fibrin sealant (Baxter Healthcare Corporation, CA) contains 36-44 mM $CaCl_2$. Thrombin solutions and tissue adhesive solutions are typically warmed before mixing, typically to 37° C.

A preparation of the present invention can be used as a topical preparation. By "topical preparation" is meant that a fibrin clot like structure is formed at a particular site on a subject, typically a tissue or wound surface. To achieve this, either a solution comprising fibrinogen and sulfated polysaccharide in the presence of a cation, e.g. calcium, and optionally a thrombin solution are mixed at the topical site, or they are mixed externally and then introduced to the topical site before clot formation is complete. An example of the latter is when the fibrin clot is used as a glue to adhere a self-supporting sheet-like material of cross-linked fibrin to a site to prevent or reduce the formation of post-surgical adhesions, as in WO 96/22115 (Baxter International Healthcare, IL). The clot must not be completely formed before the sheet-like material is introduced to the topical site, or the material will not adhere to the site. A clot formed in situ by the method of the first aspect of the invention might be used as adjunct to hemostasis in surgeries involving cardiopulmonary bypass and treatment of spleen injuries due to blunt or penetrating trauma to the abdomen, or as an adjunct in the closure of a colostomy.

The fibrin clot like structure may be used, for example, as a substrate for the culture of adherent cells, particularly mammalian cells, for enhancing hemostasis or for tissue gluing or sealing.

In a third aspect the present invention provides a hemostatic patch comprising
(1) a carrier, and
(2) at least one hemostatic agent which is a sulfated polysaccharide, wherein, if the carrier is a sulfated polysaccharide, it is not the same sulfated polysaccharide as the hemostatic agent.

The carrier is a biocompatible material such as e.g. selected from the group consisting of collagen, gelatin, fibrinogen, fibrin and a polysaccharide, or derivatives or mixtures thereof. Preferably collagen or a derivative thereof is used.

Polysaccharides include for example cellulose and derivatives thereof, such as e.g. methylcellulose, carboxymethylcellulose, oxidised cellulose, chitin, chitosan, chondroitin, hyaluronic acid, starch etc.

The term "derivative" includes substances which are chemically or physically, e.g. by heat treatment, modified.

Preferably the sulfated polysaccharide is present in an amount of from 20 ng to 3 mg for every $cm^2$ of active surface of the hemostatic patch.

The sulfated polysaccharide may be present on an active surface of the hemostatic patch or is distributed within a matrix of the hemostatic patch.

The patch may further comprise thrombin and fibrinogen on an active surface of the hemostatic patch.

By "hemostatic patch" is meant a carrier optionally comprising one or more hemostatic agents which, when applied to the surface of a wound, promotes hemostasis. According to the present invention, the hemostatic patch comprises a hemostatic agent which is a sulfated polysaccharide. By "hemostatic agent" is meant an agent which can promote hemostasis, for example an antifibrinolytic agent, or clot promoting agent. The carrier is typically solid, but may alternatively be a gel. Suitable carriers are described in U.S. Pat. No. 6,733,774 B2 (Stimmeder; Nycomed Pharma AS) and U.S. Pat. No. 7,399,483 B2 (Stimmeder; Nycomed Pharma AS) and include collagen sponges, and carriers made from a biodegradable polymer such as polyhyaluronic acid, polyhydroxy acid, e.g. lactic acid, glucolic acid, hydroxybutanoic acid, a cellulose or gelatine. Such carriers are typically flexible, have a density of 1-10 mg/cm$^3$ and have an elasticity module of 5-100 N/cm$^2$. Particularly preferred carriers are enzymatically degraded within about 4 to 6 months after application, avoiding the need for surgical removal. Typically, the carrier is in the form of a fiber, including microfibers, a fabric, a foam or a gel. The carrier may be a sulfated polysaccharide, such as sulfated cellulose. However, it may be the same sulfated polysaccharide as the hemostatic agent which is a sulfated polysaccharide.

Suitably, according to the third aspect of the present invention, if the carrier comprises a sulfated polysaccharide, it is not the same sulfated polysaccharide as the hemostatic agent.

The preparation of a coated carrier may consist essentially of the preparation of a suspension of the active ingredients, even distribution of the suspension on the carrier, drying of the coated carrier to a solid composition or gel/fixation of the active ingredients to the carrier. The suspension typically comprises particles having a mean diameter of 25-100 μm. Suspensions of sulfated polysaccharides are typically prepared in organic solvents. A method of evenly distributing a suspension on a carrier is disclosed in U.S. Pat. No. 5,942,278 (Hagedorn et al, Nycomed Arzneimittel GmbH, DE). A method of coating a carrier with fibrinogen and thrombin is disclosed in U.S. Pat. No. 6,733,774 B2. These methods could readily be adapted by the skilled person to obtain a hemostatic patch comprising a sulfated polysaccharide.

Alternatively, covalent linking of sulfated polysaccharides to the fibers of a hemostatic patch, such as an oxidised cellulose sheet, may be performed. Means of performing this covalent linkage are well known in the art. For example, US 2004/0101546 (Gorman and Pendharkar) describes the covalent linkage of hemostatic agents to an oxidised, aldehyde-modified cellulose patch.

As an alternative, or in addition to surface coating of the hemostatic patch, the sulfated polysaccharide may be distributed throughout the hemostatic patch. For example, a solid carrier could be soaked in a solution of the sulfated polysaccharide and subsequently dried. Alternatively, a solution or suspension of the sulfated polysaccharide could be combined with a solution of a monomer, which is then polymerised to form the solid carrier with the sulfated polysaccharide distributed evenly throughout. For example, a sulfated polysaccharide could be dissolved together with acid soluble collagen at pH 2-3. Upon neutralization, a collagen gel made of a network of collagen fibers, containing the sulfated polysaccharide in the liquid phase of the gel, is formed. After freeze-drying of the collagen gel, a hemostatic patch comprising a spongy collagen pad containing sulfated polysaccharides evenly distributed within the pad is obtained. The preparation of acid-soluble collagen monomer, and it precipitation at neutral pH and lyophilisation are described in U.S. Pat. No. 6,773,699 (Tissue Adhesive Technologies, Inc). Collagen membranes are reviewed in Bunyaratavej P and Wang H L (2001) J. Periodontol. 72:215-29.

An alternative carrier is the self-supporting sheet-like material of cross-linked fibrin disclosed in WO96/22115 (Delmotte and Krack; Baxter International Healthcare, IL). Typically, such a carrier is used as a bio-mechanical barrier in the treatment of internal, traumatic lesions, particularly for the prevention of adhesion formation as a post-operative complication. When the carrier contains a sulfated polysaccharide according to the ninth aspect of the invention, it may have hemostatic properties.

The presence of the sulfated polysaccharide increases the effectiveness of the hemostatic patch in hemostasis. As described herein, sulfated polysaccharides promote fibrin generation, and so may promote clot formation at a wound surface. Fibrinogen and thrombin may be available at the wound surface, or may be added exogenously. Suitably, the sulfated polysaccharide is present in a quantity which affects the formation of a fibrin clot by promoting thrombin-mediated fibrin generation. The hemostatic patch is more effective in promoting hemostasis than is a hemostatic patch lacking the sulfated polysaccharide, but of otherwise similar composition. The effectiveness of the hemostatic patch in hemostasis may be tested in relation to experimental wounds in animals, such as according to tests described in U.S. Pat. No. 6,733,774 B2. For example, 48 hours following incision and puncture of the spleen or resection of the tip of the cranial liver lobe in dogs, necroscopy may be performed and evidence of secondary hemorrhage sought by gross observation and histological examination. A hemostatic patch may be applied to an experimental spleen lesion in pigs, and time to cessation of hemorrhage measured.

Typically, the sulfated polysaccharide is present on the active surface of the hemostatic patch, typically in an amount of from 20 ng to 3 mg/cm$^2$, typically from 0.2 to 300 μg/cm$^2$, for example from 3 to 300 μg/cm$^2$. For example, the carrier may be coated with the sulfated polysaccharide. Typically, the sulfated polysaccharide is in a solid form and is evenly distributed and fixed upon the carrier.

Alternatively, the sulfated polysaccharide is distributed within the matrix of the hemostatic patch, typically in an amount of from 20 ng to 3 mg for every cm$^2$ of the active surface of the hemostatic patch, typically from 0.2 to 300 μg/cm$^2$, for example from 3 to 300 μg/cm$^2$. The "matrix" of the hemostatic patch is the part or parts of the carrier which terminate in an active surface. If the matrix has a depth of 1 cm, the sulfated polysaccharide is typically present in an amount of from 20 ng/cm$^3$ to 3 mg/cm$^3$ of the matrix. If the matrix has a depth of 1 mm, the sulfated polysaccharide is typically present in an amount of from 200 ng/cm$^3$ to 30 mg/cm$^3$ of the matrix.

It will be understood that the sulfated polysaccharide may be distributed in the matrix of the hemostatic patch, and also present on the active surface. In that case, the combined sulfated polysaccharide on the active surface and in the matrix is typically from 20 ng to 3 mg for every cm$^2$ of the active surface, and typically from 0.2 to 300 μg/cm$^2$, for example from 3 to 300 μg/cm$^2$.

The hemostatic patch may contain no agents which promote hemostasis other than the sulfated polysaccharide.

Alternatively, it may contain one or more other active agents, for examples antifibrinolytic agents, or agents which promote clotting. In a preferred embodiment, an active surface of the hemostatic patch further comprises thrombin and fibrinogen. Suitably, the thrombin is present in an amount of 1.0-5.5 IU/cm$^2$, preferably about 2.0 IU/cm$^2$, and the fibrinogen is present in an amount of 2-10 mg/cm$^2$, preferably 4.3-6.7 mg/cm$^2$. A method for making a hemostatic patch comprising thrombin and fibrinogen is disclosed in U.S. Pat. No. 6,733,774 B2.

In a further aspect the present invention provides a method of tissue sealing or tissue gluing comprising applying on a wound surface a hemostatic patch according to the third aspect of the invention.

In a further aspect the present invention provides a method of obtaining hemostasis, comprising applying on an area of blood leakage a hemostatic patch according to the third aspect of the invention.

The hemostatic patch of the present invention is useful for hemostasis, tissue gluing and tissue sealing, in particular in surgical intervention in the gastrointestinal system, such as the esophagus, stomach, small intestine, large intestine, rectum, on parenchymal organs, such as liver, spleen, pancreas, kidneys, lungs, adrenal glands, thyroid and lymph nodes, cardiovascular surgery, thoracic surgery including surgery on the trachea, bronchi or lungs, surgical interventions in the ear, nose and throat (ENT) area including dental surgery, gynecological, urological, bone (e.g. spongiosa resection), and emergency surgery, neurological surgery, lymphatic, biliary, and cerebrospinal (CSF) fistulae, and air leakages during thoracic and pulmonary surgery. The present invention thus also relates to the use of the hemostatic patch of the ninth aspect of the invention for the above purposes. Further, the hemostatic patch may be substantially liquid tight, making it highly useful in surgery of highly bleeding organs such as the liver and spleen, and for surgery e.g. in the gastrointestinal channel. The hemostatic patch of the present invention is typically to be applied when bleeding cannot be controlled with conventional methods or when these methods would yield unfavorable results.

In a further aspect the present invention provides a method of making a hemostatic patch according to the present invention, comprising coating a carrier with a sulfated polysaccharide and/or distributing a sulfated polysaccharide within a carrier. Suitable methods are as described above.

In a fourth aspect the present invention provides a two-component syringe system comprising EITHER
(a) the one component composition of claim 1 in the first barrel, and
(b) a cation containing preparation, optionally together with thrombin, in the second barrel; OR
(a') the separated sulfated polysaccharide of claim 1 and a cation-containing preparation, optionally together with thrombin in the first barrel, and
(b') a fibrinogen preparation in the second barrel.

In another aspect the present invention provides a syringe comprising a thrombin solution in one barrel, a fibrinogen containing solution in a second barrel and a solution of sulfated polysaccharide in a third barrel and calcium ions either in the thrombin or in the sulfated polysaccharide solution.

In a fifth aspect the present invention provides the use of a preparation of the present invention, a fibrin clot like structure of the present invention or a patch of the present invention for enhancing hemostasis.

In a sixth aspect the present invention provides the use of a preparation of the present invention, a fibrin clot like structure of the present invention or a patch of the present invention for wound healing.

In a seventh aspect the present invention provides the use of a preparation of the present invention, a fibrin clot like structure of the present invention or a patch of the present invention for use as a drug delivery system.

In an eighth aspect the present invention provides a method of tissue sealing or tissue gluing comprising applying on a wound surface a preparation of the present invention, a fibrin clot like structure of the present invention or a patch of the present invention.

In another aspect the present invention provides an in vitro surface coated with a clot formed in vitro according to the method of the present invention. The in vitro surface may be used as a substrate for the culture of adherent cells, particularly mammalian cells.

US 2006/134093 (Ronfard; DFB Pharmaceuticals Inc, US) discloses fibrin cell supports for cell cultures formed by the mixture of fibrinogen and thrombin. The fibrin cell supports may be used for preparing a culture of cells such as keratinocytes, recovering the culture in the form of a reconstituted tissue, and transporting same. The reconstituted tissue is particularly suitable for use as a skin graft. The clot and in vitro surface of the seventh and eighth aspect of the inventions may be used as disclosed in US 2006/134093. Suitable surfaces may consist of a synthetic membrane made from one or more of the following materials (polyester, PTFE or polyurethane); from one or more biodegradable polymers (e.g., hyaluronic acid, polylactic acid or collagen); or a silicone or Vaseline gauze dressing, or any other material suitable for wound dressing.

In any of the aspects of the invention, it is preferred that the sulfated polysaccharide is a non-anticoagulant sulfated polysaccharide (NASP). "NASP" as used herein refers to a sulfated polysaccharide that exhibits anticoagulant activity in a dilute prothrombin time (dPT) or activated partial thromboplastin time (aPTT) clotting assay that is no more than one-third, and preferably less than one-tenth, the molar anticoagulant (statistically significant increase in clotting time) activity of unfractionated heparin (MW range 8,000 to 30,000; mean 18,000 daltons). NASPs may be purified and/or modified from natural sources (e.g. brown algae, tree bark, animal tissue) or may be synthesized de novo and may range in molecular weight from 100 daltons to 1,000,000 daltons. A reduced tendency towards an anti-coagulant effect in vivo, compared to sulfated polysaccharides which are not NASPs, is desirable as a precautionary measure, as any risk of an anti-coagulant effect to a patient is thereby minimized. In any case, fibrin sealants and hemostatic patches are intended only for topical use, and so the leakage of the sulfated polysaccharide into the blood system should be gradual, minimizing any undesired anti-coagulant effects. Therefore, sulfated polysaccharides having anti-coagulant effects may be used, particularly at low concentrations.

NASPs are "non-anticoagulant," in that they do not significantly increase clotting times over the range of concentrations studied. Sulfated polysaccharides with potential NASP activity include, but are not limited to, glycosaminoglycans (GAGs), heparin-like molecules including N-acetyl heparin (Sigma-Aldrich, St. Louis, Mo.) and N-desulfated heparin (Sigma-Aldrich), sulfatoids, polysulfated oligosaccharides (Karst et al. (2003) Curr. Med. Chem. 10:1993-2031; Kuszmann et al. (2004) Pharmazie. 59:344-348), chondroitin sulfates (Sigma-Aldrich), dermatan sulfate (Celsus Laboratories Cincinnati, Ohio), fucoidan (Sigma-Aldrich), pentosan polysulfate (PPS) (Ortho-McNeil Pharmaceuticals, Raritan, N.J.), fucopyranon sulfates (Katzman et al. (1973) J. Biol. Chem. 248:50-55), and novel sulfatoids such as GM1474 (Williams et al. (1998) General Pharmacology 30:337) and SR 80258A (Burg et al. (1997) Laboratory Investigation 76:505), and novel heparinoids, and their analogs. NASPs may be purified and/or modified from natural sources (e.g. brown algae, tree bark, animal tissue) or may be synthesized de novo and may range in molecular weight from 100 daltons to 1,000,000 daltons. Additional compounds with potential NASP activity include periodate-oxidized heparin (POH) (Neoparin, Inc., San Leandro, Calif.), chemically sulfated laminarin (CSL) (Sigma-Aldrich), chemically sulfated alginic acid (CSAA) (Sigma-Aldrich), chemically sulfated pectin (CSP) (Sigma-Aldrich), dextran sulfate (DXS) (Sigma-Aldrich), heparin-derived oligosaccharides (HDO) (Neoparin, Inc., San Leandro, Calif.).

Preferred NASPs are fucoidan and pentosan polysulfate. Fucoidan is a polysaccharide composed largely of sulfated esters of fucose, with a variable degree of branching. Linkages may be predominantly $\alpha(1 \to 2)$ or $\alpha(1 \to 3)$. $\alpha(1 \to 4)$ linkages may also be present. The fucose esters are predominantly sulfated at position 4 and/or 2 and/or 3. Monosulfated fucoses dominate, although desulfated fucose may also be present. In addition to sulfated fucose esters, fucoidan may also contain non-sulfated fucose, D-xylose, D-galactose, uronic acid, glucuronic acid or combinations of more than one of these. F-fucoidan is >95% composed of sulfated esters of fucose, whereas U-fucoidan is approximately 20% glucuronic acid.

The present invention also provides a method of preparation of a fibrin clot comprising mixing a tissue adhesive solution comprising fibrinogen with a thrombin solution in the presence of calcium ions and a sulfated polysaccharide.

In especial, the presence of the sulfated polysaccharide causes an increase in the clot opacity of the fibrin clot.

In a preferred aspect the method is for a topical preparation of a fibrin clot.

In a preferred aspect the tissue adhesive solution comprises sulfated polysaccharide, e.g. at a concentration of between 1.2 µg/ml and 20 mg/ml, such as between 0.6 µg/ml and 10 mg/ml in a composition formed upon mixing of the tissue adhesive solution and the thrombin solution.

In a preferred aspect the tissue adhesive solution and the thrombin solution are each provided in a separate syringe barrel of a multiple-barrelled syringe.

The present invention also provides a fibrinogen preparation comprising a sulfated polysaccharide.

Preferably the fibrinogen preparation is one, wherein a tissue adhesive solution comprising the fibrinogen preparation is capable of forming a fibrin clot in no more than 10 minutes at 37® C. upon mixing with an equal volume of a solution comprising 4 IU thrombin and 40 µmol $CaCl_2$ per ml.

The fibrinogen preparation of the present invention comprises preferably 0.01 µg to 300 µg sulfated polysaccharide for every mg of fibrinogen.

The present invention also provides a thrombin preparation comprising a sulfated polysaccharide.

The thrombin preparation is preferably one wherein a thrombin solution comprising the thrombin preparation is capable of causing a tissue adhesive solution comprising 50 mg/ml fibrinogen to form a fibrin clot in no more than 10 minutes at 37® C. upon mixing with an equal volume of the tissue adhesive solution, wherein either solution comprises calcium ions, preferably the thrombin preparation comprises from 1.2 ng to 20 mg sulfated polysaccharide for every IU of thrombin.

In another aspect the fibrinogen preparation or the thrombin preparation of the present invention is a lyophilised preparation or a frozen solution.

The present invention also provides a syringe comprising a tissue adhesive solution comprising the fibrinogen preparation of the present invention in one barrel.

The syringe preferably comprises a further barrel comprising a thrombin solution.

In another aspect the present invention provides a syringe comprising a thrombin solution in one barrel, a tissue adhesive solution in a second barrel and a solution of sulfated polysaccharide in a third barrel.

The present invention also provides a clot formed according to the method of described above.

The present invention further provides an in vitro surface coated with a clot formed according to the method of the present invention.

The present invention also provides
  a method of tissue sealing or tissue gluing comprising applying on a wound surface a hemostatic patch according to the present invention;
  a method of obtaining hemostasis, comprising applying on an area of blood leakage a hemostatic patch of the present invention,
  a method of making the hemostatic patch of the present invention comprising coating a carrier with a sulfated polysaccharide and/or distributing a sulfated polysaccharide within a carrier,
  the use of a sulfated polysaccharide to provide a hemostatic function in a hemostatic patch, e.g. a patch as of the present invention, Preferably the sulfated polysaccharide in the preparations above, in the patch above and for the methods and uses is a non-anticoagulant sulfated polysaccharide (NASP).

DESCRIPTION OF THE FIGURES

FIG. 1A-1C: Turbidity and appearance of clot-like aggregates obtained at constant fibrinogen concentration (50 mg/ml) and various concentration of fucoidans and $Ca^{2+}$-ions.

Concentrations: fibrinogen 2.5 mg/ml; thrombin 0.125 IU/ml

The present invention will be further illustrated in the following examples without any limitation thereto.

EXAMPLE 1

Figure 1:
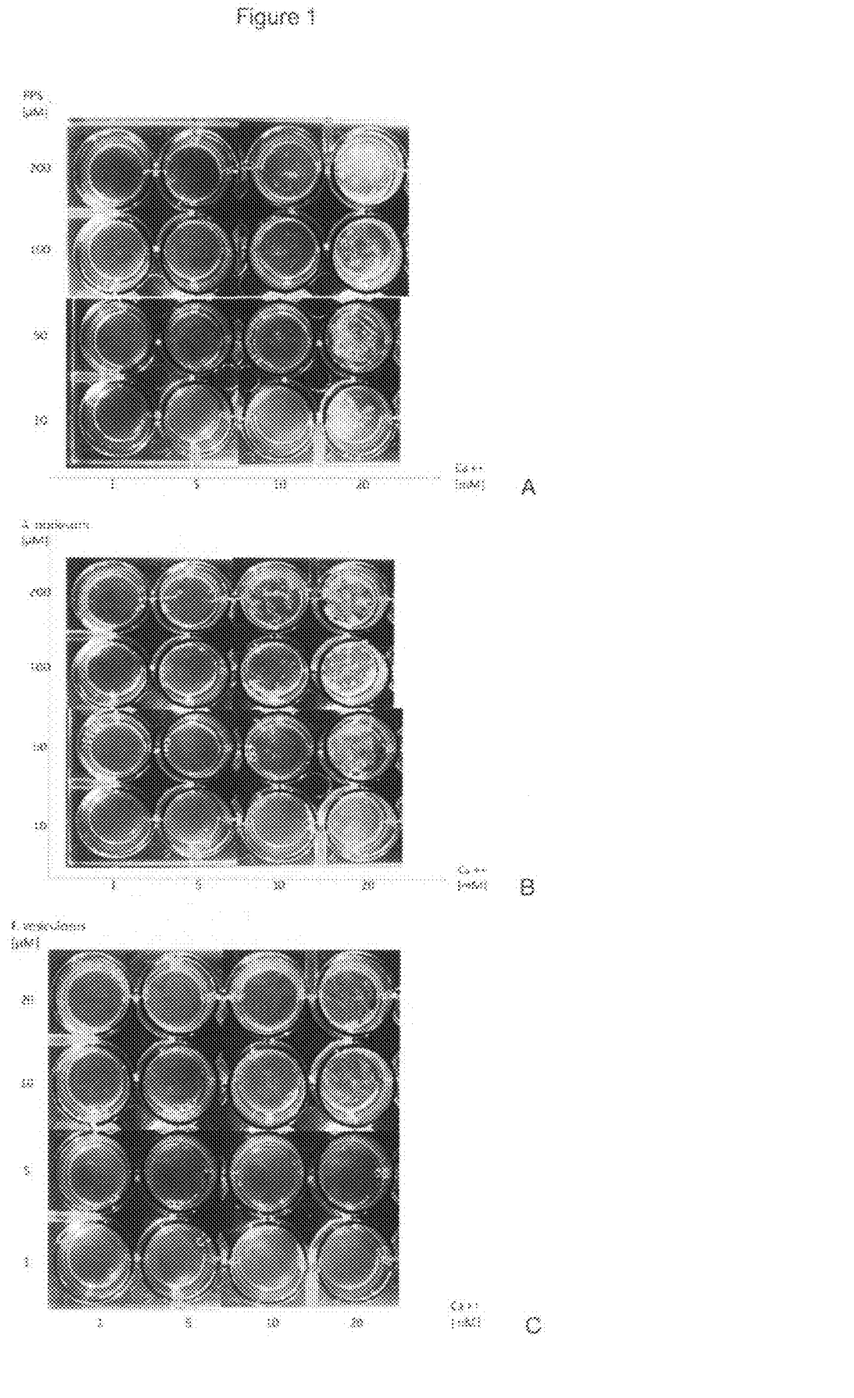

Surprisingly we have observed that at high fibrinogen concentration, in the presence of fucoidans and $Ca^{2+}$-ions macroscopically gel-like aggregates are rapidly formed. All these three compounds are necessary to obtain these self assembling aggregates. The consistency of the material obtained at a fibrinogen concentration of 50 mg/ml changes from light opalescence to clot-like appearance with increasing fucoidan and $Ca^{2+}$-ion concentration (FIG. 1A-1C). In the experiments 0.5 ml Tisseel VH S/D sealer protein solution with the designated concentration of fucoidan is first placed in the wells of a 24 well cell culture plate. 0.5 ml of a solution of $CaCl_2$ are added to attain the final concentrations indicated in FIG. 1 and rapidly mixed with the fibrinogen solution. The turbidity and consistency of the obtained mixture are evaluated. At the constant fibrinogen concentration of 50 mg/ml the turbidity of the mixture is increasing with increasing fucoidan or pentosanpolysulfat concentration. However this increase is strongly $Ca^{2+}$-ion dependent. It is low at 1 mM $Ca^{2+}$-concentration but pronounced at 20 mM $Ca^{2+}$-concentration. The mixtures obtained at the high concentrations of fucoidans/pentosanpolyphosphate and $Ca^{2+}$ are gel-like and adhering to the walls of the cell culture plates, whereas those obtained at the low concentrations have the consistency of viscous fluids. Both, the fucoidan/pentosanpolysulfate and $Ca^{2+}$-ions are necessary at higher concentrations in order to obtain a gel-like material. The lack of homogeneity of the mixture obtained at the higher concentrations of fucoidan/pentosanpolysulfate and $Ca^{2+}$-ion can be explained by poor mixing due to a too fast setting by self-assembling and the inclusions of air bubbles.

EXAMPLE 2

Figure 2:
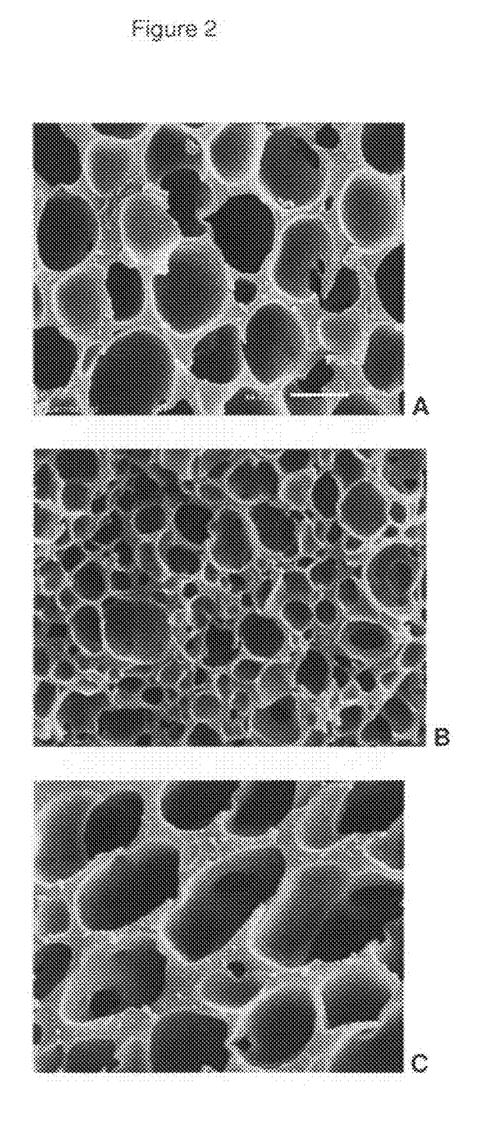
FIG. 2: Ultrastructure of gel-like materials obtained from the mixture of fibrinogen, fucoidan/pentosanpolysulfate and $Ca^{2+}$-ions. Concentrations: fibrinogen, 50 mg/ml; $Ca^{2+}$, 20 mM; Pentosanpolysulfate (A), 200 µM; A. nodosum LMW fucoidan (B), 200 µM; *Fucus vesiculosus* fucoidan (C), 20 µM. The bar represents 5 µm.
Figure 5:
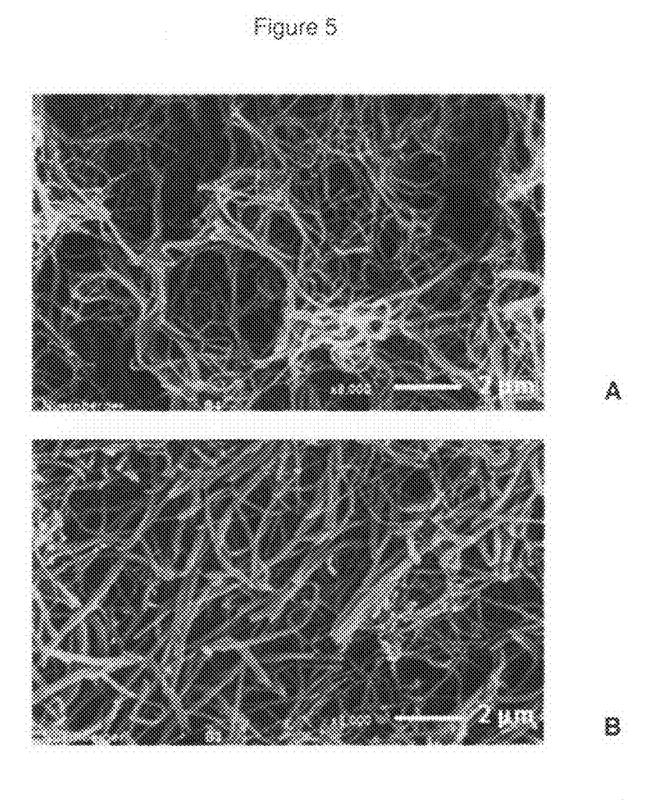
FIG. 5: Scanning electron microscopy of fibrin clots obtained from diluted Tisseel VH S/D fibrin sealant without added fucoidan (A) and with 1 µM *Fucus vesiculosus* fucoidan (B).

The structure of the gel-like materials obtained at the highest concentrations of fucoidan/pentosanpolysulfate and $Ca^{2+}$-ions in example 1 (upper right in FIGS. 1A, B, and C) is analyzed by scanning electron microscopy (SEM). After the clot forming time of 1.5 hours at 37® C. the clots are transferred in a fixation solution consisting of 2.5% glutaraldehyde in 0.1 cacodylate buffer at pH 7.3. The weight ratio of clot to fixation solution is 1:10. After 12 hours at 4® C. the clots are washed 3 times with 0.1M cacodylate buffer pH 7.3 using the same weight ratio as before. Post-fixation is carried out in 0.5% osmium tetroxide containing 1% potassium ferrocyanide for 2 hours. The clots are washed in distilled water and dehydrated with 2.2 dimethoxypropane. The samples are transferred into acetone and broken in liquid nitrogen. Samples are chemically dried with hexamethyldisilazane, mounted on stubs and coated with a palladium-gold alloy. The images obtained are shown in FIG. 2. It is evident that the novel gel-like material obtained by the combination of fibrinogen, fucoidan/pentosanpolysulfate and $Ca^{2+}$-ions has a very different organization compared to the fibrin clots shown in FIG. 5A. In the fast and spontaneous self assembling process which starts with bringing together the three compounds a three dimensional structure of adhering vesicles is formed.

EXAMPLE 3

Figure 3:
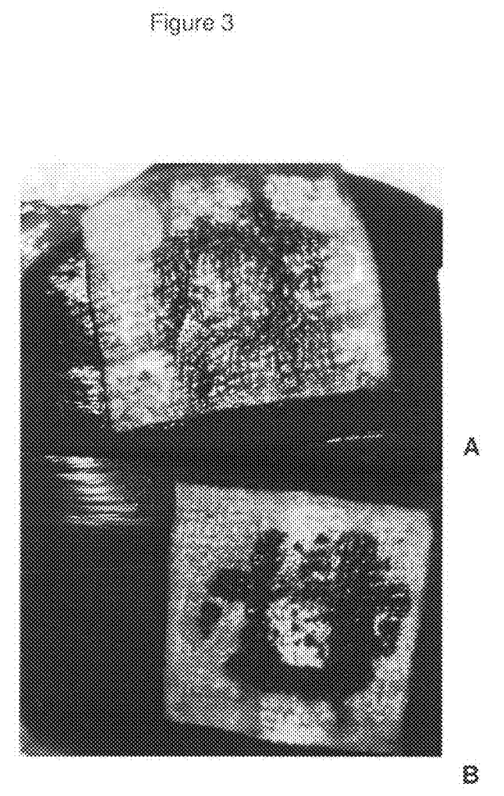
FIG. 3: Hemostatic effect of a A. nodosum fucoidan/$CaCl_2$-containing collagen pad (B) compared to the pure collagen pad (MATRISTYPT®️ collagen pad) (A) in a liver surface abrasion model on heparinized rabbits. The pictures are taken 15 minutes after the pad applications onto the bleeding wound.

Due to the observed properties of fucoidans in combination with $Ca^{2+}$-ions to form a gel-like material together with fibrinogen a hemostatic pad based on collagen is prepared. The idea behind is that these additives contained in the collagen pad can interact with the blood fibrinogen, and thus enhance the hemostatic properties of the collagen pad. A collagen sponge of 2 mm thickness (MATRISTYPT® collagen pad, Dr. Suwelack, Germany) is soaked with a solution containing A. nodosum LMW fucoidan and $CaCl_2$ and freeze-dried. The soaking solution contains the ingredients in a concentration such that after freeze-drying concentrations of 0.3 mg/cm² A. nodosum LMW fucoidan and 0.9 mg/cm² $CaCl_2$ are obtained in the pad. The pad is applied in a rabbit hemostasis model to assess its hemostatic properties. The rabbits are heparinized with 1000 IU/kg body weight. With a grinding rotating tool a circular bleeding (diameter 1.8 cm) is set by abrasion of the liver capsule. This wound is treated with the pad described above. The dry pad is applied onto the bleeding wound. The pad is pressed against the wound with the aid of saline soaked gauze for 2 minutes. As a control MATRISTYPT® collagen pad is applied onto another liver lobe of the same animal in the same manner. The experiments are run in duplicate with a second animal. The outcome is the same in both animals and is exemplarily shown for one animal in FIG. 3. As can be observed from FIG. 3, the blood soaked into the collagen pad containing fucoidan and $CaCl_2$ appears darker than in the control. This can be explained by faster coagulation in the pad caused by the action of the ingredients.

EXAMPLE 4

Figure 4:
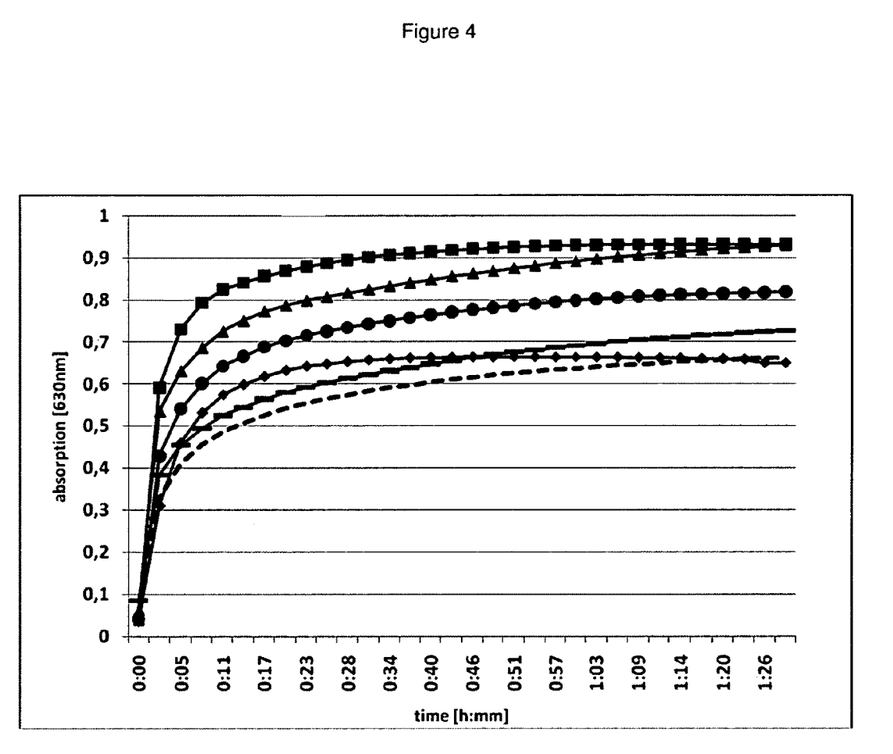
FIG. 4: Influence of fucoidans on the turbidity during fibrin clot formation. Concentration during clot formation: Fibrinogen (diluted Tisseel VH S/D): 2.5 mg/ml; Thrombin 0.125 IU/ml. PPS—pentosanpolysulfat, 10 µM; FAN—fucoidan A. nodosum, LMW: 10 µM, HMW: 0.1 µM; FLJ—fucoidan *Laminaria japonica*, 0.1 µM; FFV—fucoidan *Fucus vesiculosus*, 1 µM.

The influence of fucoidans on the kinetics of turbidity increase during the thrombin catalyzed fibrin clot formation and the final turbidity of the obtained clots is additionally confirmed using diluted fibrin sealant Tisseel VH S/D (Baxter) as fibrinogen substrate. Tisseel VH S/D sealer protein solution is diluted 1/20 (corresponding to a fibrinogen concentration of 5 mg/ml) and the fucoidan concentrations adjusted to 20 µM (pentosanpolysulfate, *Ascophyllum nodosum* LMW), 2 µM (*Fucus vesiculosus*), and 0.2 µM (*Ascophyllum nodosum* HMW, *Laminaria japonica*). 100 µl of these diluted Tisseel VH S/D solutions (containing fibrinogen, fibronectin and factor XIII) are mixed in wells of a 96 well microplate with 100 µl 0.25 IU/ml thrombin solution (Baxter) containing 40 mM $CaCl_2$. The measurement of turbidity increase during clot formation at 37® C. is recorded at 630 nm over a time period of 1.5 hours after mixing. The results are shown in FIG. 4. It is observed that some fucoidans but also pentosanpolysulfat can accelerate the thrombin catalyzed clot formation reaction and influence the formation of fibrin clots with an increased turbidity.

EXAMPLE 5

Increased turbidity of fibrin clots is associated with "coarse" clots, i.e. fibrin clots with an increased fiber diameter (Oenick MD Studies on fibrin polymerization and fibrin structure—a retrospective. Biophys Chem. 2004 Dec. 20; 112(2-3):187-92).

Fibrin clots with the fucoidan from *Fucus vesiculosus* and without fucoidan are prepared as described in example 4. The preparation of the samples for SEM is performed as described in Example 2.

EXAMPLE 6

An assay for studying thrombin mediated fibrin formation and the effect of sulfated polysaccharides on this process has been developed. Briefly, clot formation is initiated in a solution containing fibrinogen by the addition of thrombin and followed spectrophotometrically. Absorbance at 405 nm is indicative of clot opacity, which depends on quantity and/or quality of the fibrin clot.

To each well of a 96 well micro-plate (polystyrene, F-bottom; Greiner Bio-One GmbH, Kremsmuenster, Austria) 55 µl of human fibrinogen (plasminogen, fibronectin, factor XIII depleted, American Diagnostica Inc., Stamford, Conn., USA) diluted in dilution buffer (25 mM Hepes pH 7.35, 175 mM NaCl, 2.5 mM $CaCl_2$, 5 mg/ml HSA) is added. The final concentration of fibrinogen in a 100 µl assay volume is 2.5 mg/ml. 10 µl of the sulfated polysaccharide test sample diluted in dilution buffer (or dilution buffer alone) is added to the mixture and incubated for 15 minutes at 37® C. on a micro-plate incubator. The fibrin clot formation is initiated by the addition of 35 µL pre-warmed human thrombin (Enzyme Research Laboratories, South Bend, Ind., USA) diluted in dilution buffer (or dilution buffer alone), pre-warmed to 37® C. The micro-plate is transferred immediately to the pre-warmed (37® C.) micro-plate reader (Safire$^{2TM}$ micro-plate reader; Tecan Trading AG, CH) and clot formation is followed at 405 nm for 60 minutes by reading every 30 second. At each time point the absorbance readings of each sample well are corrected by subtraction of the readings of wells containing just fibrinogen.

In an initial experiment, the concentration of thrombin is varied from 0.1 to 8 nM and sulfated polysaccharides are not included in the assay. The absorbance at 405 nm increases rapidly initially but reaches a plateau at between about 20 and 30 minutes. The $A_{405}$ at 60 minutes is recorded for each of the thrombin concentrations. Results are shown in Table 1 below.

TABLE 1

| | Thrombin (nM)* | | | | |
|---|---|---|---|---|---|
| | 0 | 0.1 | 0.5 | 2 | 8 |
| $A_{405}$ at 60 minutes | 0.0000 | 0.012 | 0.034 | 0.045 | 0.053 |

*Concentrations represent the final concentration in the assay.

There is an approximately linear relationship between thrombin concentration and $A_{405}$ at 60 minutes for concentrations of thrombin of 0 to 0.5 nM. Increasing the thrombin concentration further does not result in a comparable increase in $A_{405}$ at 60 minutes. Accordingly, a concentration of 0.5 nM thrombin is chosen for further experiments.

EXAMPLE 7

The influence of different concentrations of each of 6 sulfated polysaccharides on thrombin mediated fibrin clot formation is examined according to the method described in Example 6. Details of the sulfated polysaccharides are given in Table 2 below.

TABLE 2

| Sulfated polysaccharide | MW (kDa) | Source |
|---|---|---|
| Pentosan polysulfate sodium (PPS) | 5.9 | CF Pharma Ltd. (Budapest, Hungary) |
| Fucoidan LMW, *Ascophyllum nodosum* | 7.5 | Kraeber GmbH & Co (Ellerbek, Germany) |
| Fucoidan, *Fucus vesiculosus* | ~115.5 | F6531; Sigma-Aldrich Chemie GmbH (Taufkirchen, Germany) |
| Fucoidan, *Undaria pinnatifida* | ~127 | Kraeber GmbH & Co (Ellerbek, Germany) |
| Fucoidan HMW, *Ascophyllum nodosum* | ~600 | Kraeber GmbH & Co (Ellerbek, Germany) |
| Fucoidan, *Laminaria japonica* | >1000 | Kraeber GmbH & Co (Ellerbek, Germany) |

In this experiment, the thrombin concentration is 0.5 nM and $A_{405}$ is recorded at 60 minutes. For each polysaccharide tested, low concentrations generally have little effect on the $A_{405}$ at 60 minutes. Raising the concentration generally results in a large increase in the $A_{405}$ at 60 minutes. The concentration at which the increase is observed varies between different polysaccharides. For example, the fucoidan from *L. japonica* causes a large increase in $A_{405}$ at 60 minutes at 100 nM. In contrast, pentosan polysulfate sodium at 100 nM has a negligible effect, but a large effect at 10000 nM. Results are shown in Table 3 below.

TABLE 3

| | Concentration (nM)* | | | | | |
|---|---|---|---|---|---|---|
| | 0 | 1 | 10 | 100 | 1 000 | 10 000 |
| Polysaccharide | $A_{405}$, 60 minutes | | | | | |
| PPS | 0.043 | | | 0.037 | 0.064 | 0.429 |
| A. nodosum LMW | 0.043 | | | 0.037 | 0.049 | 0.234 |
| F. vesiculosus | 0.043 | | 0.048 | 0.058 | 0.237 | |
| U. pinnatifida | 0.043 | | 0.044 | 0.046 | 0.058 | |
| A. nodosum HMW | 0.043 | 0.042 | 0.040 | 0.113 | | |
| L. japonica | 0.043 | 0.042 | 0.054 | 0.163 | | |

*Concentrations represent the final concentration in the assay.

Although the nM concentration at which the sulfated polysaccharides stimulate fibrin clot formation varies widely, the concentrations in µg/ml that cause the $A_{405}$ at 60 minutes to at least double in the assay compared to the assay in the absence of sulfated polysaccharides are roughly comparable between the different polysaccharides. Results are shown in Table 4 below.

TABLE 4

| | Concentration at which $A_{405}$, 60 min is at least double in the presence compared with the absence of polysaccharide. | |
|---|---|---|
| Sulfated polysaccharide | Conc (nM) | Conc (µg/ml) |
| PPS | 10,000 | 59 |
| A nodosum LMW | 10,000 | 75 |
| F. vesiculosus | 1000 | 116 |
| U. pinnatifida | — | — |
| A. nodosum HMW | 100 | 60 |
| L japonica | 100 | 100 |

High concentrations of the sulfated polysaccharides, i.e. in the range of about 50-100 µg/ml, generally cause an increase in clot opacity at a thrombin concentration of 0.5 nM that is greater than the increase that is observed in Example 6 by the use of 8 nM thrombin. Results therefore suggest that clot opacity (and hence fibrin generation and/or clot quality) can be improved by sulfated polysaccharides in a manner which cannot be simulated by increasing thrombin concentration.

EXAMPLE 8

Sulfated polysaccharides may be included in fibrin sealants in order to improve thrombin dependent fibrin generation. A suitable fibrin sealant that may be modified by the inclusion of sulfated polysaccharides is the TISSEEL® fibrin sealant from Baxter Healthcare Corporation (CA, USA). This is the most preferred embodiment of the invention.

Sealer protein solution is made up by dissolving the sealer protein concentrate in fibrinolysis inhibitor solution at 37® C. using a warming and stirring device such as FIBRINOTHERM® warming and stirring device in the usual way. However, a quantity of sulfated polysaccharide may be included in the sealer protein concentrate or fibrinolysis inhibitor solution, to give a final concentration in the sealer protein solution in the range of 100 to 200 µg/ml. Thrombin is reconstituted in $CaCl_2$ solution to make thrombin solution in the usual way. Each of the solutions is drawn into one of the two syringe bodies of the DUPLOJECT® syringe ready for use. The fibrin sealant may be prepared ready for use by other methods, for example it may be stored as a frozen pre-filled syringe, and defrosted ready for use. Any of the methods appropriate for preparing TISSEEL® fibrin sealant is appropriate.

The ready for use fibrin sealant may be used by a health care professional, for example to control bleeding. Upon mixing of the solutions during expulsion from the Duploject® syringe, the sulfated polysaccharide will be present in the mixture at a concentration range of 100 to 200 µg/ml in order to improve fibrin generation. The fibrin sealant may be applied as a thin layer to a dried wound surface and the sealed parts held or fixed in the desired position for about three to five minutes.

The fibrin sealant may be used in any indication for which TISSEEL® fibrin sealant is suitable. For example, it may be used as adjunct to hemostasis in surgeries involving cardiopulmonary bypass and treatment of spleen injuries due to blunt or penetrating trauma to the abdomen. Alternatively, it may be used as an adjunct in the closure of a colostomy.

As an alternative to including the sulfated polysaccharide in the sealer protein solution component, it may be included in the thrombin solution.

TISSEEL® fibrin sealant usually contains aprotinin to preclude premature fibrinolysis. However, some individuals are hypersensitive to aprotinin. It may be possible to include sulfated polysaccharide in the TISSEEL® fibrin sealant and omit the aprotinin for use in such individuals. The increased fibrin generation or improved clot quality mediated by the sulfated polysaccharide may render the use of aprotinin unnecessary.

EXAMPLE 9

Sulfated polysaccharides may be included within a hemostatic patch, in order to improve thrombin dependent fibrin generation.

For example, the self-supporting sheet-like material of cross-linked fibrin disclosed in WO 96/22115 (Delmotte and Krack; Baxter International Healthcare, IL) may be soaked in a solution of sulfated polysaccharide, typically at a concentration of 100 to 200 µg/ml. The fibrin sheet is allowed to dry under sterile conditions and is stored for future use.

The fibrin sheet may subsequently be used by a surgeon to treat an internal traumatic lesion, such as a spleen lesion, by applying the fibrin sheet to the wound surface, optionally with a layer of TISSEEL® fibrin sealant between the fibrin sheet and the wound surface. The sulfated polysaccharide will promote clot formation, thus reducing hemorrhage, and the fibrin sheet prevents the development of adhesions.

The invention claimed is:

1. A gel-like aggregate organized as a self-assembled three dimensional structure of adhering vesicles, the three dimensional structure obtained by a process comprising the steps of:
   providing a preparation comprising fibrinogen in an amount of 60 mg/ml to 120 mg/ml in a solution and a sulfated polysaccharide;
   providing a cation containing solution as a separate component; and
   mixing the fibrinogen and sulfated polysaccharide preparation and the cation containing solution so that the gel-like aggregate is obtained,
   wherein the process does not involve the action of thrombin,
   wherein:
      the gel-like aggregate includes the fibrinogen, the sulfated polysaccharide, and the cation, and
      the gel-like aggregate does not comprise thrombin.

2. A gel-like aggregate obtained by a process comprising the steps of:
   providing a preparation comprising fibrinogen as a solution;
   providing a cation containing solution as a separate component together with a sulfated polysaccharide; and
   mixing the fibrinogen preparation and the solution containing the cation and the sulfated polysaccharide so that the gel-like aggregate is obtained,
   wherein the process does not involve the action of thrombin,
   wherein:
      the gel-like aggregate includes the fibrinogen, the sulfated polysaccharide, and the cation,
      the gel-like aggregate does not comprise thrombin, and
      the fibrinogen is present in the gel-like aggregate in a three dimensional arrangement of adhering vesicles.

3. The gel-like aggregate of claim 1, wherein the sulfated polysaccharide is a fucoidan.

4. The gel-like aggregate of claim 1, wherein the sulfated polysaccharide is a fucoidan selected from the group consisting of *Ascophyllum nodosom* LMW fucoidan, *Ascophyllum nodosom* HMW fucoidan, *Fucus vesiculosus* fucoidan, *Undaria pinnatifida* fucoidan, and *Laminaria japonica* fucoidan.

5. The gel-like aggregate of claim 1, wherein the cation is selected from the group consisting of calcium, magnesium, barium, and strontium.

6. The gel-like aggregate of claim 1, wherein the cation is provided from calcium chloride.

7. The gel-like aggregate of claim 1, wherein the sulfated polysaccharide is selected from the group consisting of glycosaminoglycans (GAGs), heparin-like molecules, sulfatoids, polysulfated oligosaccharides, chondroitin sulfates, dermatan sulfate, fucoidan, pentosan polysulfate (PPS), fucopyranon sulfates, heparinoids, periodate-oxidized heparin (POH), sulfated laminarin (SL), sulfated alginic acid (SAA), sulfated pectin (SP), dextran sulfate (DXS), and heparin-derived oligosaccharides (HDO).

8. The gel-like aggregate of claim 7, wherein the heparin-like molecules comprise N-acetyl heparin or N-desulfated heparin.

9. The gel-like aggregate of claim 2, wherein the sulfated polysaccharide is a fucoidan.

10. The gel-like aggregate of claim 2, wherein the sulfated polysaccharide is a fucoidan selected from the group consisting of *Ascophyllum nodosom* LMW fucoidan, *Ascophyllum nodosom* HMW fucoidan, *Fucus vesiculosus* fucoidan, *Undaria pinnatifida* fucoidan, and *Laminaria japonica* fucoidan.

11. The gel-like aggregate of claim 2, wherein the cation is selected from the group consisting of calcium, magnesium, barium, and strontium.

12. The gel-like aggregate of claim 2, wherein the cation is provided from calcium chloride.

13. The gel-like aggregate of claim 2, wherein the sulfated polysaccharide is selected from the group consisting of glycosaminoglycans (GAGs), heparin-like molecules, sulfatoids, polysulfated oligosaccharides, chondroitin sulfates, dermatan sulfate, fucoidan, pentosan polysulfate (PPS), fucopyranon sulfates, heparinoids, periodate oxidized heparin (POH), sulfated laminarin (SL), sulfated alginic acid (SAA), sulfated pectin (SP), dextran sulfate (DXS), and heparin-derived oligosaccharides (HDO).

14. The gel-like aggregate of claim 13, wherein the heparin-like molecules comprise N-acetyl heparin or N-desulfated heparin.

15. The gel-like aggregate of claim 1, wherein the cation is at least divalent.

16. The gel-like aggregate of claim 2, wherein the cation is at least divalent.

17. The gel-like aggregate of claim 2, wherein the fibrinogen as a solution has a concentration of 60 mg/ml to 120 mg/ml.

18. The gel-like aggregate of claim 1, wherein the sulfated polysaccharide is present in an amount of 0.01 µg to 300 µg sulfated polysaccharide for each milligram of fibrinogen.

19. The gel-like aggregate of claim 2, wherein the sulfated polysaccharide is present in an amount of 0.01 µg to 300 µg sulfated polysaccharide for each milligram of fibrinogen.

20. The gel-like aggregate of claim 1, wherein the sulfated polysaccharide is distributed homogeneously in the three dimensional structure.

21. The gel-like aggregate of claim 2, wherein the sulfated polysaccharide is distributed homogeneously in the three dimensional structure.

22. The gel-like aggregate of claim 2, wherein the fibrinogen in the preparation has a concentration of 50 mg/ml.

23. The gel-like aggregate of claim 1, wherein the gel-like aggregate has a clot like appearance.

24. The gel-like aggregate of claim 2, wherein the gel-like aggregate has a clot like appearance.

25. The gel-like aggregate of claim 1, wherein the cation containing solution comprises water.

26. The gel-like aggregate of claim 2, wherein cation containing solution comprises water.

27. The gel-like aggregate of claim 1, wherein the solution comprises water.

28. The gel-like aggregate of claim 2, wherein the solution comprises water.

29. The gel-like aggregate of claim 1, wherein the cation in the cation containing solution has a concentration of 20 mM.

30. The gel-like aggregate of claim 2, wherein the cation in the cation containing solution has a concentration of 20 mM.

31. The gel-like aggregate of claim 1, wherein the sulfated polysaccharide has a concentration from 20 µM to 200 µM in the preparation.

32. The gel-like aggregate of claim 2, wherein the sulfated polysaccharide has a concentration of 20 µM to 200 µM in the preparation.

* * * * *